United States Patent [19]

Arganbright et al.

[11] Patent Number: 5,446,231
[45] Date of Patent: Aug. 29, 1995

[54] METHOD FOR REMOVING CONTAMINANTS FROM HYDROCARBON STREAMS

[75] Inventors: Robert P. Arganbright, Seabrook; Edward M. Jones, Jr., Friendswood; Dennis Hearn, Houston, all of Tex.

[73] Assignee: Chemical Research & Licensing Company, Pasadena, Tex.

[21] Appl. No.: 185,121

[22] Filed: Jan. 24, 1994

[51] Int. Cl.$^6$ ............................ C07C 7/00; C07C 7/10
[52] U.S. Cl. .................................. 585/802; 585/833; 585/864
[58] Field of Search .................. 585/802, 864, 833

[56] References Cited

U.S. PATENT DOCUMENTS

| | | | |
|---|---|---|---|
| 4,211,638 | 7/1980 | Akell et al. | 208/180 |
| 4,351,970 | 9/1982 | Sommer et al. | 568/895 |
| 4,490,563 | 12/1984 | Pool et al. | 568/697 |
| 4,556,461 | 12/1985 | Ogura et al. | 203/29 |
| 4,665,237 | 5/1987 | Arakawa et al. | 568/697 |
| 5,352,848 | 10/1994 | Cottrell | 568/699 |

FOREIGN PATENT DOCUMENTS 0047906  3/1982  European Pat. Off.

OTHER PUBLICATIONS

Smith et al "New MTBE Design Now Commercial", Hydrocarbon Processing, Mar. 1982 pp. 121–122.
Kirk–Othermer "Encyclopedia of Chemical Technology" second completely Revised edition, 1964 John Wiley & Sons, Inc, p. 806.
Petroleum Processing Handbook, McGraw–Hill Book Co., 1967 p. 3–58.
ION Exchange Resin Catalyzed Addition of Alcohols to Olefins, Ancillotti, et al, Jr. of Catalysis 46, 49–57 (1977).

Primary Examiner—Sharon A. Gibson
Assistant Examiner—Nhat D. Phan
Attorney, Agent, or Firm—Kenneth H. Johnson

[57] ABSTRACT

The present invention is a method for removing nitrile contaminants from $C_5$ streams. In particular, a $C_5$ stream is washed in a countercurrent fashion with a mixture comprising 50% methanol and 50% water to extract the nitriles from the $C_5$ hydrocarbons into the water-methanol mixture. Propionitrile removal is enhanced by the presence of the methanol in the solvent. An further embodiments include (1) a method for recovering methanol from the extract stream by hydrogenating the nitriles to form amines, converting the amines to ammonium salts by acid treatment and distilling out the methanol and (2) distilling out methanol/nitriles from the extract stream, admixing the methanol/nitriles with an alkane/alkene/ether stream then distilling the methanol out in a azeotrope with the alkane/alkenes while leaving the nitriles in the ether.

17 Claims, 3 Drawing Sheets

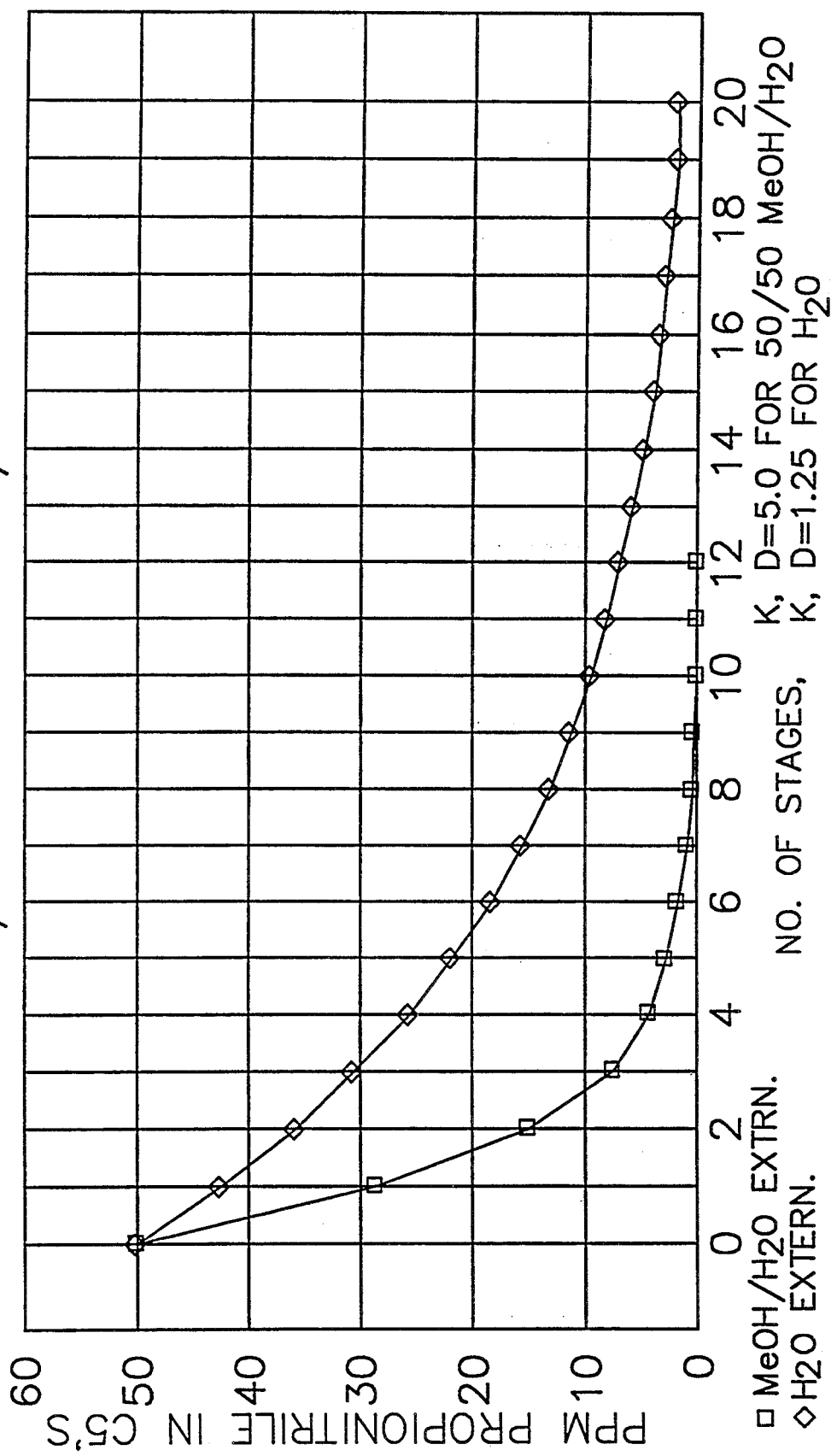

METHOD FOR REMOVING CONTAMINANTS FROM HYDROCARBON STREAMS

BACKGROUND OF THE INVENTION

1. Field of the Invention

The present invention relates to a method for removing contaminants from a hydrocarbon feed stream to an etherification reactor. More particularly, the invention relates to a process for nitriles from hydrocarbon feed streams.

2. Related Information

Since the Clean Air Act Amendments of 1990 refiners have searched for ways to introduce oxygen into gasoline to produce cleaner burning reformulated fuels. In addition to methyl tertiary butyl ether (MTBE), other suitable ethers for this purpose are tertiary amyl methyl ether (TAME) and ethyl tertiary butyl ether (ETBE).

Manufacturers are looking for alternative sources of hydrocarbons for the production of ethers and oxygenates. These sources include $C_5$ hydrocarbons which contain isoamylenes that are suitable for the production of TAME.

TAME is formed by the reaction of isoamylene and methanol at mild operating conditions over an acid catalyst. The selectivity of this reaction is limited by equilibrium constraints. By using a catalytic distillation column, essentially complete conversion is attainable.

The reaction of an alcohol and an olefin and concurrent separation of the reactants from the reaction products by fractional distillation has been practiced for some time. The process is variously described in U.S. Pat. Nos. 4,232,177; 4,307,254; 4,336,407; 4,504,687; 4,987,807; and 5,118,873 all commonly assigned herewith.

Briefly the alcohol and isoolefin are fed to a distillation column reactor having a distillation reaction zone containing a suitable catalyst, such as an acid cation exchange resin, in the form of catalytic distillation structure. As embodied in the etherification of isoamylene's the olefin and an excess of methanol are first fed to a fixed bed reactor wherein most of the olefin is reacted to form the corresponding ether, tertiary amyl methyl ether (TAME). The fixed bed reactor is operated at a given pressure such that the reaction mixture is at the boiling point, thereby removing the exothermic heat of reaction by vaporization of the mixture. The fixed bed reactor and process are described more completely in U.S. Pat. No. 4,950,803 which is hereby incorporated by reference.

The effluent from the fixed bed reactor is then fed to the distillation column reactor wherein the remainder of the isoamylenes are converted to the ether and the methanol is separated from the ether which is withdrawn as bottoms. The $C_5$ olefin stream generally contains only about 10 to 60 percent olefin, the remainder being inerts which are removed in the overheads from the distillation column reactor. The overhead hydrocarbon raffinate contains an amount of methanol up to the azeotropic concentration of about 12 wt %.

This stream is washed with water to separate methanol from the hydrocarbons. Methanol is then distilled to remove the water. In this invention a portion of the water-methanol extract is first used as a solvent to extract nitriles from the $C_5$ feed before it is sent to a distillation tower.

The etherification processes typically utilize strongly acidic ion exchange resins as etherification catalysts, which are strongly acidic organic polymers. As an isobutylene or isoamylene molecule meets alcohol at an active site, the reaction takes place rapidly forming ether.

The activity of the catalyst for etherification reactions is a function of the acid loading or capacity of the resin. This functionality is not linear; a loss of 20% of acid sites on the catalyst gives approximately 50% loss of activity for conversion to ether. It is therefore important to minimize the deactivation of the catalyst with effective feed pretreatment to maintain peak performance and long catalyst life. The loss of catalytic activity may be caused by the adsorption of basic compounds or metal ions, the blockage of the active sites by polymeric products, or by the splitting off the functional groups due to long term operation at temperatures above 240° F. The latter two causes are affected by the operating conditions of the etherification reactor. The major source of lost activity is typically from poisons entering with the feedstocks to the unit. Poisons to the catalyst include basic compounds such as ammonia, amines, caustic soda, and nitriles. In particular, acetonitrile (ACN) and propionitrile (PN) have been found to deactivate the catalyst.

In refinery applications, the largest source of hydrocarbon feedstock containing isoolefins is the stream from the fluidized catalytic cracking unit (FCCU). Some $C_4$ and $C_5$'s are also obtained from fluid or delayed cokers. Nitriles are formed in these units that enters the etherification process with the hydrocarbon feed stream. The amount of nitriles in the feed varies with the severity of the catalytic cracker operation, crude source, and catalyst used in the FCCU. Propionitrile has been found to be a particular problem in the $C_5$ stream. Unlike all the other feed poisons which deactivate the catalyst in a plug flow fashion through the catalyst bed, nitrile's deactivation mechanism is not immediate and results in a diffused deactivation throughout the entire bed. No effective means has been found to reactivate the catalyst.

In order to obtain adequate run lengths with the catalyst and optimum performance, the first step in the etherification process is a feed pretreatment step designed to remove the poisons to very low levels (<1 ppm). Since the poisons are much more soluble in water than hydrocarbon, the common treatment is a multistage water wash either in countercurrent or concurrent systems. The water and hydrocarbon streams are contacted utilizing trays or packing. In the countercurrent tower the continuous water phase flows down the column as the liquid hydrocarbon droplets are dispersed upwards. The design variables include the number of theoretical contact stages and the flow rate of water.

Normally, nitriles are removed from $C_4$ and $C_5$ hydrocarbon streams by washing the hydrocarbon stream with water to extract the nitriles into the water phase. This works well with acetonitrile but is much less effective with propionitrile.

It is an advantage of the present invention to provide an improved method for the removal of nitriles from hydrocarbon streams, in particular $C_5$ streams. It is a particular feature of the present process that propionitrile removal from the $C_5$ streams is enhanced.

SUMMARY OF THE INVENTION

The present invention is a method for removing nitrile contaminants from hydrocarbon streams. In particular, a hydrocarbon stream is washed with a mixture comprising water and 20 to 80 wt %, preferably and 30 to 60 (more preferably up to 50 wt %) alcohol to extract the nitriles from the hydrocarbons into the water-alcohol mixture. It has been found that the presence of alcohol in the solvent enhances the nitrile extraction, especially the propionitrile. The present nitrile removal process is particularly useful to remove propionitrile (PN) from isoamylene containing $C_5$ streams used to produce TAME. Similarly the present process is useful for the removal of acetonitrile from $C_4$ streams. Although other alcohols may be useful, methanol and ethanol are preferred.

Briefly stated, the present method for extracting nitriles from hydrocarbon streams comprises:

(a) passing a hydrocarbon stream comprising hydrocarbons and nitrile contaminants to an extraction column;

(b) passing a solvent stream comprising a mixture of alcohol and water to said extraction column;

(c) removing an extract stream comprising substantially the mixture of alcohol and water and the nitrile contaminants;

(d) removing a raffinate stream comprising said hydrocarbons substantially free of the nitrile contaminants.

Extraction processes are often used when distillation is difficult or ineffective. Extraction utilizes differences in the solubilities of the components rather than differences in their volatilities. Extraction takes advantage of chemical differences between components rather than vapor pressure differences as in distillation.

Liquid-liquid extraction is the separation of constituents of a liquid solution by contact with another insoluble liquid. If the substances comprising the original solution distribute themselves differently between the two liquid phases, a certain degree of separation will result, and this may be enhanced by the use of multiple contacts or stages.

The solution which is to be extracted is called the feed and the liquid with which the feed is contacted is the solvent. The solvent-rich product of the operation is called the extract, and the residual liquid from which solute has been removed is raffinate.

In liquid-liquid extraction two phases must be brought into intimate contact to permit transfer of material and then be separated. Extraction equipment may be operated batchwise or continuously. A quantity of feed liquid may be mixed with a quantity of solvent in an agitated vessel, after which the layers are settled and separated into extract and raffinate. This gives about one theoretical contact (stage), which may be adequate in simple extractions. This operation may be repeated if more than one contact is required, but when the quantities involved are large and several contacts are needed, continuous flow becomes economical. Most extraction equipment is continuous, with either successive stage contacts or differential contacts. Types of equipment used in a liquid extraction are mixer-settlers, vertical towers of various kinds which operate by gravity flow, agitated tower extractors, and centrifugal extractors.

One method of measuring the efficiency of an extraction is the distribution coefficient (K). The distribution coefficient (K) represents the amount of the contaminant in the extract divided by the amount of the contaminant in the raffinate. The distribution coefficient for propionitrile in a water/methanol solvent represents the amount of PN in the extract (Water+Methanol+PN) divided by the amount of PN in the raffinate (HC+PN).

An alternative embodiment of the present invention includes a method for recovering alcohol from the extract stream. The extract stream contains alcohol, $H_2O$ and extracted nitriles. The nitriles are removed by a process that involves first hydrogenating the extract stream to react the nitriles to amines, then acid treating the extract stream to convert the amines to their corresponding salts. The resulting mixture of alcohol, $H_2O$, and salts are easily separated by distillation, with the alcohol recovered overhead and the $H_2O$ and salt removed as bottoms product. The recovered alcohol may be fed to an appropriate etherification reactor or recycled back for further use in the liquid-liquid extraction column.

Briefly stated, one method for recovering alcohol from an extract stream comprises:

(a) passing a hydrogen stream and an extract stream comprising alcohol, water, and nitrile contaminants to a reactor to produce a reactor effluent stream where substantially all of said nitrile contaminants are converted to amines;

(b) passing said reactor effluent stream and an acid stream to an acid treater to produce an acid treater effluent stream where substantially all of said amines are converted to ammonium salts;

(c) passing said acid treater effluent stream to a distillation column for separation, said distillation column having an overheads product comprising substantially nitrile free alcohol and a bottoms product comprising water and ammonium salts.

Although the present nitrile removal and alcohol recovery are described herein in a an environment of catalytic distillation, the systems described herein above are valuable for straight pass reaction systems, where the entire feed stream passes through the catalyst bed, such as the liquid phase fixed bed reactors (e.g., U.S. Pat. No. 3,121,124) the boiling point reactor (e.g., U.S. Pat. No. 4,950,803) and moving beds (e.g., U.S. Pat. No. 5,118,872). However, in a particularly resourceful utilization of catalytic distillation the alcohol is separated from the entrained nitriles by distilling the alcohol from the water and introducing the recovered alcohol fraction into the catalytic distillation at a point below the catalyst zone. When the alcohol is separated from the water by distillation, the nitriles go overhead with the alcohol. By feeding the alcohol below the catalyst zone in the catalytic distillation column reactor, the alcohol forms a lower boiling azeotrope with the hydrocarbons, which is easily separated from the higher boiling nitriles which leave as bottoms with the ether product. The recovered alcohol is carried into the catalyst zone, where it becomes a reactant for the etherification reaction.

BRIEF DESCRIPTION OF THE DRAWINGS

FIG. 3 is a plot comparing the theoretical stages of methanol/water to water alone in propionitrile extraction.

DETAILED DESCRIPTION OF THE PREFERRED EMBODIMENTS

Refinery streams are usually separated by fractional distillation. A "light naphtha" cut is one such refinery stream and because they often contain compounds that are very close in boiling points, such separations are not precise. A $C_5$ stream, for instance, may contain $C_4$'s and up to $C_8$'s and higher. These components may be saturated (alkanes), unsaturated (mono-olefins), or polyunsaturated (diolefins). Additionally, the components may be any or all of the various isomers of the individual compounds. This mixture can easily contain 150 to 200 components, including the nitrile contaminants. Other hydrocarbon streams of $C_4$ to $C_9$ carbon atoms may be utilized in the present process.

Figure 1:
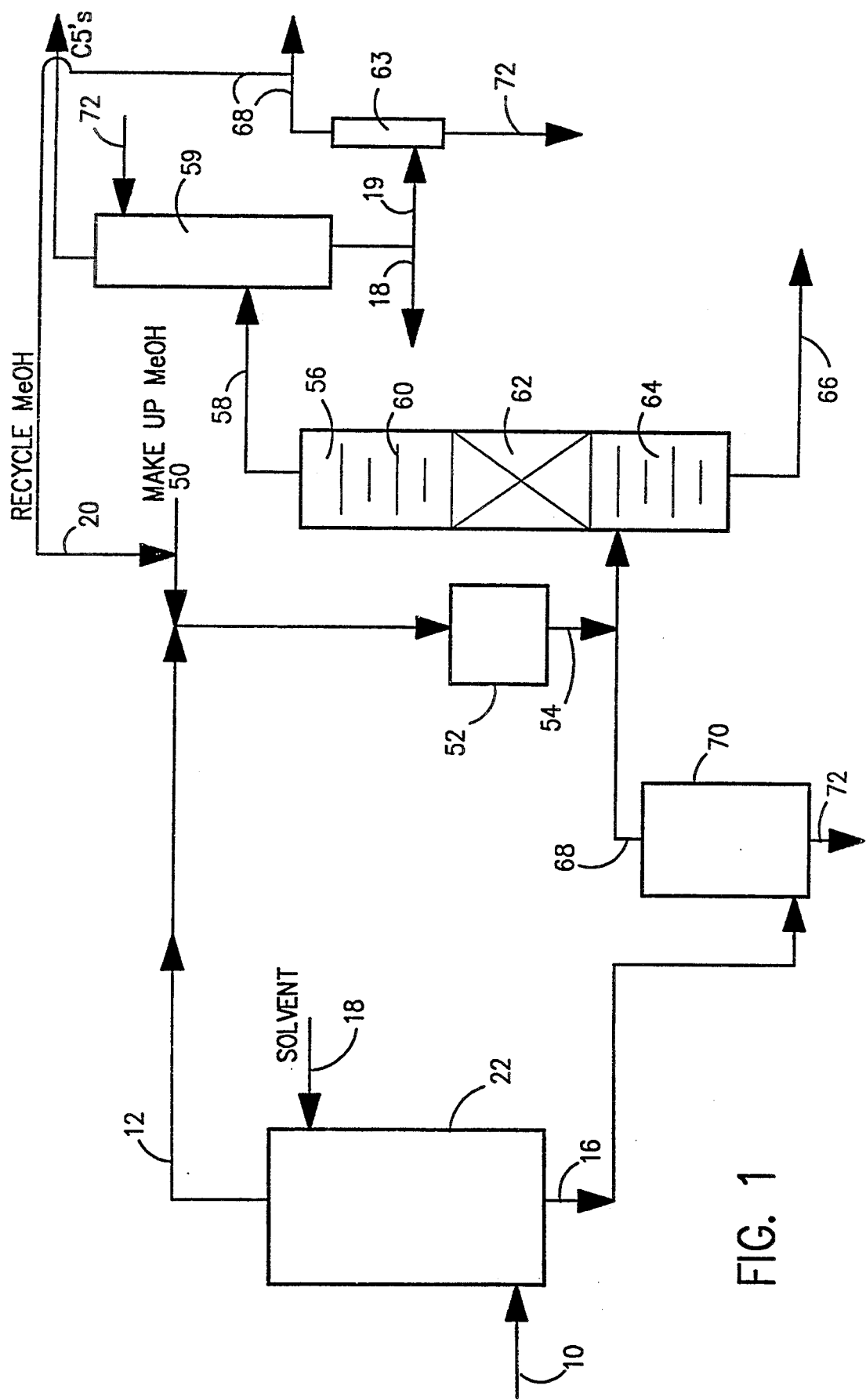
FIG. 1 is a simplified flow diagram of a two stage liquid-liquid extraction according to the invention and an alcohol recovery embodiment.

In the figures, similar elements have been given the same designation. Conventional items, such as, reflux, reboilers, valves, and the like have not been shown; however their usual utilization would be obvious to those in the art. FIG. 1 shows a two stage liquid-liquid extraction process for the removal of nitrile impurities from a $C_5$ hydrocarbon stream. The feed 10 comprising predominantly $C_5$ hydrocarbons and nitrile contaminants enters the lower portion of the liquid-liquid extraction column 22. The solvent 18 comprising a mixture of 50% methanol and 50% water enters the upper portion of the liquid-liquid extraction column 22, countercurrent to the feed 10. Typically, the lower density liquid is fed to the lower portion of the column, while the higher density liquid is fed to the upper portion of the column to effect a countercurrent separation. The liquid-liquid extraction column 22 may be an open vessel, packed tower, or a multistage tower.

Since, the nitriles are more soluble in the water-methanol mixture than the hydrocarbon phase, they are extracted into the water-methanol mixture. The first extractant 16 comprising water, methanol and extracted nitriles exits the liquid-liquid extraction column 22. The first raffinate 12 comprises predominantly $C_5$ hydrocarbons with only a small amount of nitriles remaining.

The solvent comprising a mixture of methanol and water may be adjusted to any concentration to effect the desired extraction efficiency.

In a further embodiment the stream 12 which is now substantially free of nitriles is used as a feed to a guard bed or guard bed reactor 52 (U.S. Pat. No. 4,950,803) after mixing with alcohol e.g. methanol from line 50 which contains fresh make up methanol and some recycle methanol sufficient to allow excess methanol to be present in reactor 52 relative to the tertiary olefin concentration. The recycle methanol is not used in the extractor and is recovered by distillation of a portion of the methanol-water extract of the catalytic distillation overhead. In order for the methanol to be in balance for the most efficient production of TAME, all of the make-up methanol plus some recycle methanol is added to the fixed bed (guard bed) reactor 52. The methanol to tertiary olefin (2-methylbutene-1 and 2-methylbutene-2) molar ratio is held at about 1.0 to 1.1. This recycle methanol is recovered from distillation tower 63 which fractionates a portion of the methanol from the water wash tower 59. This methanol does not contain propionitrile. The proportion of the extract needed to be distilled for recycle 20 to guard bed 52 is about 20% of the total extract. The remaining 80% is recycled via line 18 to wash the $C_5$ feed in extractor 22.

A methanol storage tank (not shown) is maintained in order to balance methanol inventory to be able to control the catalytic distillation tower concentration of methanol at its azeotropic concentration in $C_5$'s below the catalyst bed.

While ethanol-water blends can be used effectively for extraction of propionitrile from a $C_5$ fraction (see Table 3), it is apparent that PN must be removed from ethanol prior to recycle to the catalytic reactor in order to protect the catalyst. In this case, hydrogenation of the nitrile to an amine as shown in example 2 for methanol solvent, would be appropriate. If the unit 52 is being used as only a sacrificial guard bed the methanol would not be fed through line 50 but could be fed directly to tower 56, say below bed 62 or into line 16.

Reactor 52 contains an acid resin catalyst and serves to react a portion of the isoolefin with the alcohol and also will serve as a guard bed for the catalyst in the catalytic distillation column. The reactor 52 may be operated according to U.S. Pat. 4,950,803 or as a liquid phase reactor. The conversion is not complete, generally below equilibrium and the product stream 54 contains unreacted isoolefin and usually some alcohol. This stream is further treated in the catalytic distillation column reactor 56 by feeding it, usually below the catalyst zone 62 containing a suitable catalyst/distillation structure for example that disclosed in U.S. Pat. No. 4,215,011. There is a conventional distillation zone 64 below the catalyst zone where product ether is removed as bottoms and the unreacted isoolefin and alcohol are distilled up into the reaction zone.

Solvent stream 16 in this embodiment is fractionated in column 70 and alcohol, e.g. methanol recovered as overhead 68 and water as bottoms 72. The nitriles distill with the alcohol because of the boiling point of the water-propionitrile azeotrope and methanol. Hence, the alcohol is now contaminated and could not be used as a feed to the reactor 52. However, it can be fed to catalytic distillation/reactor column 56 at a point below catalyst zone. The alcohol forms an azeotrope with the hydrocarbons and is distilled into the catalyst zone. The nitriles on the other hand do not enter into the azeotrope and remain in the ether product 66. These levels of nitriles are in full compliance with all environmental standards for fuel. There is usually a conventional distillation zone 60 above the catalyst zone where the unreacted components of the feed (usually normal olefins and alkanes) are recovered as overhead 59.

The net effect of this embodiment is to hold the nitriles out of contact with the cation resin catalyst and to return them to the stream from whence they came after its conversion to the higher octane ether all at very little additional capital and operating cost which is more than recovered by the extended catalyst life.

Figure 2:
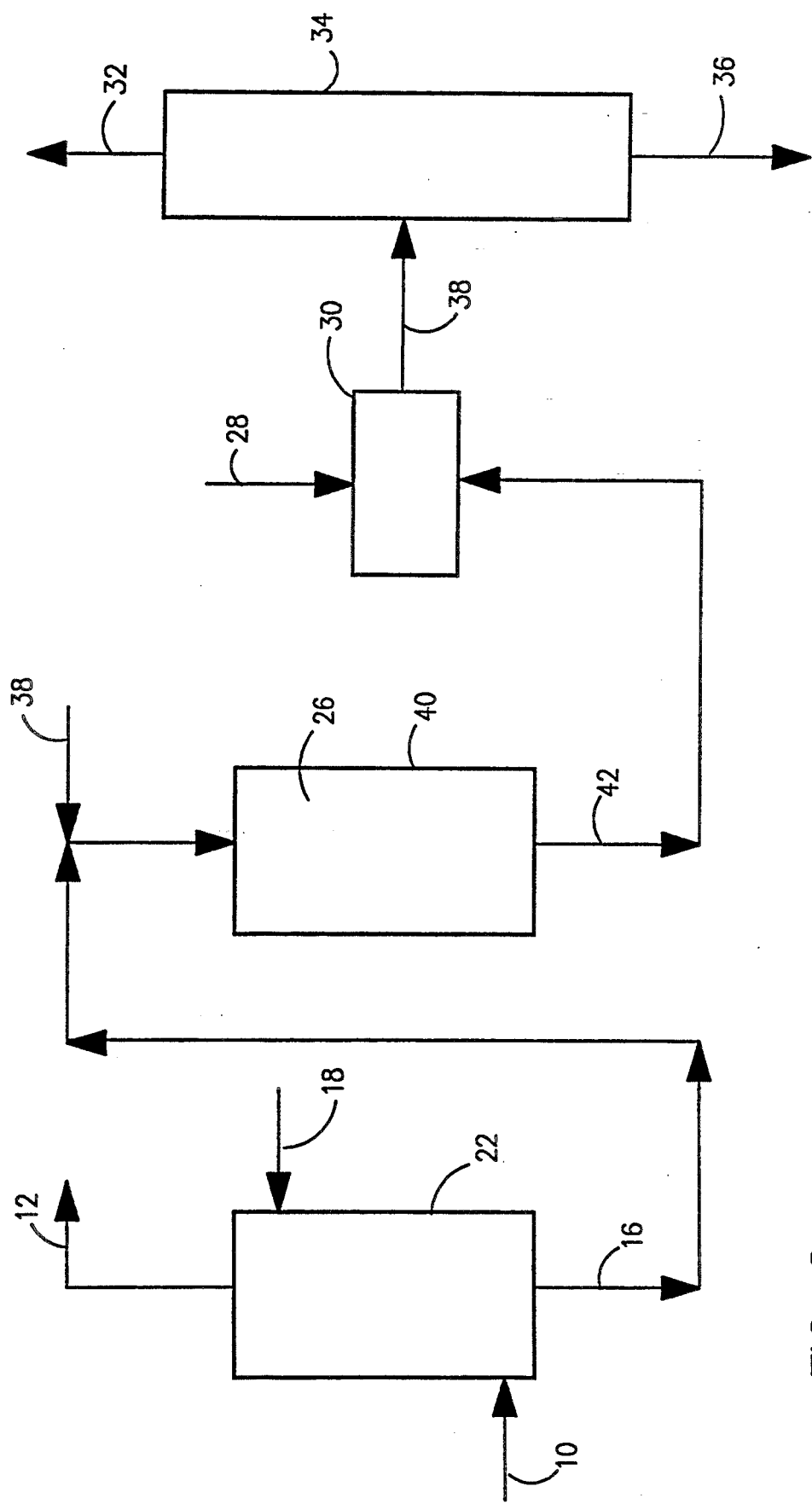
FIG. 2 is an alternative alcohol recovery embodiment of the invention including a hydrogenation and acid treatment of the recovered water/alcohol solvent.

FIG. 2 shows an embodiment of the present invention that includes an alternative method for recovering methanol from the extract stream. An extraction section as shown in FIG. 1 is used for the removal of nitrile impurities from a $C_5$ hydrocarbon stream. The extraction column is a multiple stage unit, and is illustrated by a single column. The feed 10 comprising predominantly $C_5$ hydrocarbons and nitrile contaminants enters the lower portion of the liquid-liquid extraction column 22. The solvent 18 comprising a mixture of 50% methanol and 50% water enters the upper portion of the liquid-liquid extraction column 22, countercurrent to the feed 10. The extractant 16 comprising water, methanol and extracted nitriles exits the liquid-liquid extraction column 22. The raffinate 12 comprises predominantly $C_5$ hydrocarbons with only a small amount of nitriles remaining. A single stage wash (not shown) can be used on the raffinate if necessary to essentially completely remove methanol from the hydrocarbon stream with the extract combined with the extract 16

To recover the methanol from the extract stream extract 16 is mixed with hydrogen 38 and sent to a hydrogenation reactor 24 for hydrogenation of the nitriles to amines. The hydrogenation reactor 40 typically comprises a fixed bed catalyst 26 of cobalt oxide promoted with zirconium oxide supported on kieselguhr. The hydrogenation reactor 24 is maintained at temperatures between 175° to 212° F. The pressure is maintained at 250 psig. The LHSV is maintained between 2.8 to 3.0. Excess hydrogen is maintained throughout the run. The reactor effluent 42 comprising predominantly, MeOH, amines, and $H_2O$ proceeds to the acid treater 30.

The reactor effluent 42 mixes with acid 28 in the acid treater 30 to convert the amines to their corresponding ammonium salts. The acid treater 30 is maintained at temperatures between 80° to 120° F. The pressure is maintained at 100 psig. The LHSV is maintained between 10 to 30. Excess acid is maintained throughout the run. Typically strong acids such as sulfuric acid and phosphoric acid are preferred. However, organic acids may used as applicable. The acid treater effluent 38 is fed to a distillation column 34 for separation of methanol from the $H_2O$ and salts. The methanol is removed from the distillation column 34 as overheads product 32 and the $H_2O$ and salts are removed as bottoms product 36.

Although the invention is illustrated in regard to $C_5$'s, other hydrocarbon streams having similar properties, e.g., $C_4$-$C_7$ streams or gasoline fractions (FCC gasoline, coker gasoline, etc.) may be employed with the alcohols to obtain the increased nitrile removal. Distribution coefficients for propionitrile and acetonitrile extraction with varied concentrations of methanol/water and with ethanol/water are shown in TABLE III.

EXAMPLE 1

A feed stream containing predominantly $C_5$ hydrocarbons and 35 ppm propionitrile (PN) was extracted in a single stage extraction. The solvent used was essentially pure water. The results from the extraction are shown in Table 1. The Distribution Coefficient (K) for the first raffinate stream using pure water was approximately 1.27.

EXAMPLE 2

The same feed stream as used in Example 1, was extracted in a single stage extractor. The solvent used was a mixture comprising 50% methanol and 50% water. The results from the extraction are shown in Table 2. The Distribution Coefficient (K) for the first raffinate stream using the 50% methanol and 50% water mixture was 5.3. When comparing the distribution coefficients (K) between Example 1 using pure water and Example 2 using the methanol-water mixture, the efficiency of the extraction is over 4 times greater for the methanol-water mixture.

Based on the measured Distribution Coefficient, the number of theoretical extraction stages was calculated for the use of 50/50 methanol/water versus the use of water alone as solvent. The results were plotted in FIG. 3 They indicate that only about 7 stages are required to obtain a raffinate having less than 1 ppm PN with the methanol/water blend(starting with hydrocarbon containing 50 ppm PN), whereas even twenty stages do not achieve that result with the same weight of water alone as solvent.

TABLE I

RESULTS FROM TWO STAGE WATER EXTRACTION

| | FEED | #1 EXTRACT | #1 RAFFINATE | #2 EXTRACT | #2 RAFFINATE |
|---|---|---|---|---|---|
| FEED, HC + PN | 100 ml. | | | | |
| SOLVENT (100% $H_2O$) | 19 ml. | | | | |
| ppm PN | 35.104 | 33.044 | 25.925 | 16.727 | 14.847 |
| TOTAL GRAMS PN | 0.0024 | 0.00063 | 0.00179 | 0.00032 | 0.0012 |
| K, (DISTRIBUTION COEFFICIENT) | | | 1.27 | | 0.954 |
| MATERIAL BALANCE | | | 101% | | 84% |

TABLE II

RESULTS FROM TWO STAGE 50/50 METHANOL-WATER EXTRACTION

| | FEED | #1 EXTRACT | #1 RAFFINATE | #2 EXTRACT | #2 RAFFINATE |
|---|---|---|---|---|---|
| FEED, HC + PN | 100 ml. | | | | |
| SOLVENT (50/50 $H_2O$/MeOH) | 19 ml. | | | | |
| ppm PN | 35.104 | 80.134 | 15.071 | 21.172 | 10.573 |
| TOTAL GRAMS PN | 0.0024 | 0.00137 | 0.00103 | 0.000402 | 0.000723 |
| K, (DISTRIBUTION COEFFICIENT) | | | 5.31 | | 2.007 |
| MATERIAL BALANCE | | | 100% | | 107% |

TABLE III

RESULTS OF EXTRACTION
FEED: $C_5$ TO $C_7$ LIGHT GASOLINE

| SOLVENT: (BY VOLUME) | PROPIONITRILE | ACETONITRILE |
|---|---|---|
| 0/100 MEOH/$H_2O$ | 1.3 | 11.0 |
| 20/80 MEOH/$H_2O$ | 1.6 | |
| 40/60 MEOH/$H_2O$ | 3.0 | 22.6 |
| 60/40 MEOH/$H_2O$ | 5.6 | |
| 80/20 MEOH/$H_2O$ | 8.2 | |
| 50/50 ETOH/$H_2O$ | 4.0 | |
| 50/30 ETOH/$H_2O$ | 10.5 | |

The invention claimed is:

1. A method for extracting nitrile contaminants from hydrocarbon streams comprising:
    (a) intimately contacting a hydrocarbon stream containing minor amounts of nitriles with a solvent comprising water and from 20 to 80 wt % methanol, and
    (b) separating said hydrocarbon from said solvent whereby a substantial portion of the nitriles are removed to the solvent.

2. The method according to claim 1 wherein said hydrocarbon stream comprises a C$_5$ cut.

3. The method according to claim 1 wherein from 30 to 50 wt % methanol is present in said solvent.

4. The method according to claim 1 wherein said nitriles comprise propionitrile.

5. The method according to claim 1 comprising
contacting said solvent containing the nitriles with hydrogen under conditions to convert substantially all of the nitriles to amines,
contacting said solvent containing the amines with an acid to convert substantially all of the amines to ammonium salt and thereafter
distilling the solvent to separate the alcohol from the water and ammonium salts.

6. The method according to claim 1 comprising
distilling said solvent containing nitriles to separate an alcohol/nitrile mixture from the water and
distilling said alcohol/nitrile mixture with an alkane/alkene/ether mixture to form an azeotrope of alcohol and alkane/alkene,
whereby said nitriles remain in and are removed with a bottoms of the distillation.

7. A method for extracting nitrile contaminants from hydrocarbon streams, comprising the steps of:
(a) passing a hydrocarbon stream comprising hydrocarbons and nitrile contaminants to a first extraction column;
(b) passing a solvent stream comprising a mixture of alcohol and water to said first extraction column;
(c) removing an extract stream comprising substantially the mixture of alcohol and water and the nitrile contaminants;
(d) removing a raffinate stream comprising said hydrocarbons substantially free of the nitrile contaminants.

8. The method of claim 7 wherein the hydrocarbon stream is flowed countercurrent to the solvent stream.

9. The method of claim 7 wherein the nitrile contaminant comprises acetonitrile, the hydrocarbon stream comprises C$_4$ hydrocarbons.

10. The method of claim 7 wherein the nitrile contaminant comprises propionitrile, the hydrocarbon stream comprises C$_5$ hydrocarbons.

11. The method of claim 8 wherein the nitrile contaminant comprises propionitrile, the hydrocarbon stream comprises C$_5$ hydrocarbons.

12. The method of claim 7 wherein the solvent comprises a mixture of 30 to 80 wt % methanol with water.

13. The method of claim 7 wherein said solvent comprises a mixture of 30 to 60 wt % ethanol.

14. The method according to claim 7 for extracting nitrile contaminants from hydrocarbon streams, further comprising one or more additional extraction columns in series wherein raffinate from each preceding extraction column is contacted with a solvent stream comprising a mixture of alcohol and water.

15. A method for extracting nitrile contaminants from hydrocarbon streams, comprising the steps of:
(a) passing a hydrocarbon stream comprising hydrocarbons and a nitrile contaminant to an extraction column;
(b) passing a solvent stream comprising a mixture of 30 to 60 wt % methanol and water to said extraction column;
(c) removing an extract stream comprising substantially the mixture of methanol and water and the nitrile contaminants;
(d) removing a raffinate stream comprising said hydrocarbons substantially free of the nitrile contaminants;
(e) passing said extract stream and a hydrogen stream to a reactor to produce a reactor effluent stream where substantially all of said nitrile contaminants are converted to amines;
(f) passing said reactor effluent stream and an acid stream to an acid treater to produce an acid treater effluent stream where substantially all of said amines are converted to ammonium salts;
(g) passing said acid treater effluent stream to a distillation column for separation, said distillation column having an overheads product comprising substantially nitrile free methanol and a bottoms product comprising water and ammonium salts.

16. The method of claim 15 wherein the nitrile contaminants comprise acetonitrile, the hydrocarbon stream comprises C$_4$ hydrocarbons.

17. The method of claim 15 wherein the nitrile contaminants comprise propionitrile, the hydrocarbon stream comprises C$_5$ hydrocarbons.

* * * * *